United States Patent [19]

Sato et al.

[11] Patent Number: 4,478,934
[45] Date of Patent: Oct. 23, 1984

[54] DETERMINATION OF ADENOSINE BY IMMUNOASSAY INVOLVING ACYLATION OF THE ADENOSINE

[75] Inventors: Tomokazu Sato, Choshi; Michio Ui, Sapporo, both of Japan

[73] Assignee: Yamasa Shoyu Kabushiki Kaisha, Chiba, Japan

[21] Appl. No.: 396,863

[22] Filed: Jul. 9, 1982

[30] Foreign Application Priority Data

Jul. 15, 1981 [JP] Japan .................................. 56-111324

[51] Int. Cl.$^3$ ............................................ G01N 33/54
[52] U.S. Cl. ........................................ 435/7; 436/527; 436/529; 436/530; 436/532; 436/533; 436/538; 436/542; 436/543; 436/547; 436/815
[58] Field of Search ............... 436/538, 542, 547, 815, 436/543, 527, 529, 530; 435/7

[56] References Cited

PUBLICATIONS

Chemical Abstracts, 96: 177182u, (May 24, 1982).

Primary Examiner—Sidney Marantz
Attorney, Agent, or Firm—Wenderoth, Lind & Ponack

[57] ABSTRACT

A method of quantative determination of adenosine by means of competitive immunoassay based on a competitive antigen-antibody reaction. In the competitive antigen-antibody reaction, an antibody is used which is obtained from an animal which has been immunized by introduction thereto of an antigen which comprises a carrier protein bonded with 2'- and 3'-hydroxyls of the adenosine through dicarboxylic acid residues, and a labelled adenosine and 2',3'-diacyladenosine which has been produced by acylation of adenosine in the sample to be assayed or in a standard solution are caused to undergo competitive reaction for the antibody whereby it has been made possible to determine adenosine quantitatively in high sensitivity and in high accuracy.

6 Claims, 1 Drawing Figure

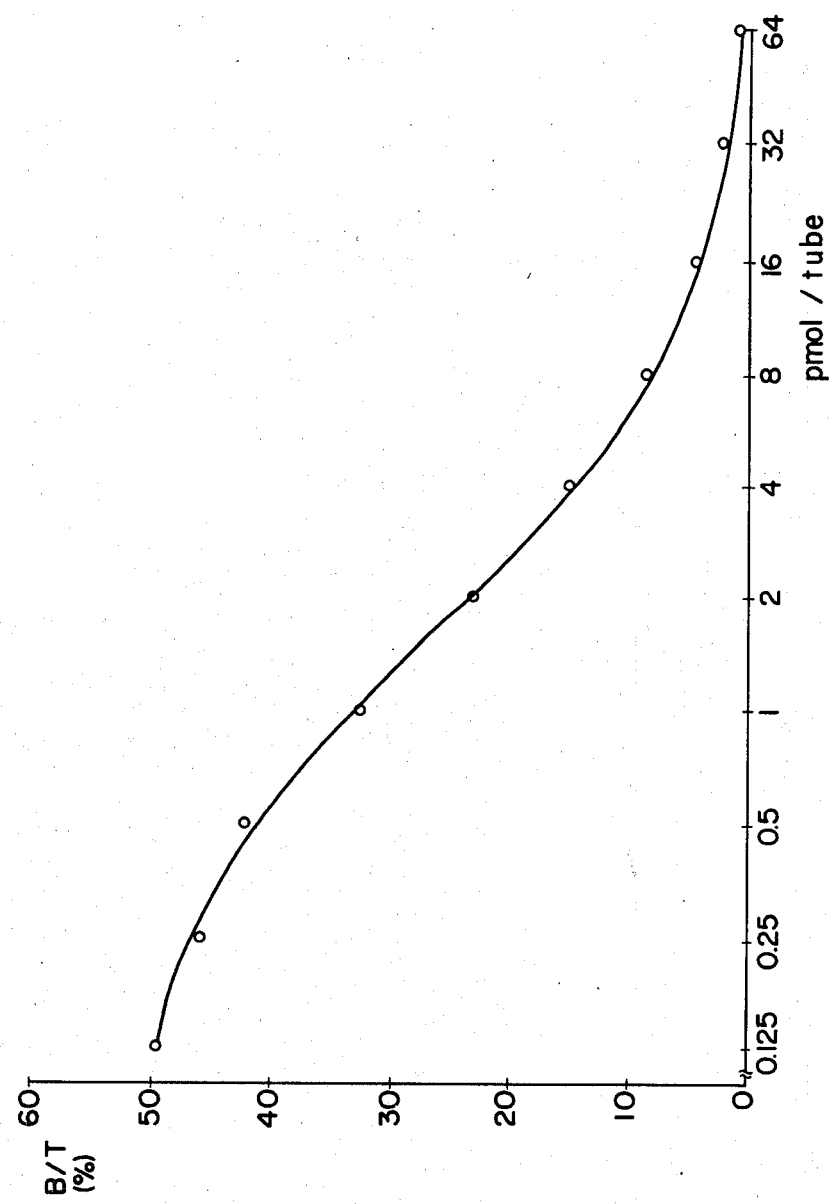

DETERMINATION OF ADENOSINE BY IMMUNOASSAY INVOLVING ACYLATION OF THE ADENOSINE

BACKGROUND OF THE INVENTION

This invention relates to quantitative determination of adenosine by immunoassay.

Adenosine has been well known in the art as one intermediate in the decomposition process of purine-type nucleic acid into nucleotide in living bodies and also as a substrate for the salvage reaction. Quite recently, based on some data, it has been suggested that adenosine may probably have some important physiological activities. Typical examples are as follows:

(1) It is probable that adenosine has a coronary circulation enhancing activity and physiologically controls the flow rate of coronary blood (*Amer. J. Physiol.* 204, p. 317, (1963)).

(2) Adenosine plays an important role in level controlling of cyclic AMP, and its effect is known to be contrariwise, namely positive or negative, depending on the types of tissues or cells (*Proc. Natl. Acad. Sci. USA*, 65, p. 1033 (1970); *J. Biol. Chem.*, 247, p. 6866 (1972); *Proc. Natl. Acad. Sci. USA*, 74, p. 5482 (1977)).

Systems in which cyclic AMP is increased: Lymphocyte, brain slice, fibroblast, blood platelet, etc.

Systems in which cyclic AMP is decreased: Lipocyte, renal cortex, hepatocyte, etc.

From these facts, it is considered probable that adenosine is secreted constantly from cells and functions to modify hormone actions.

(3) As to the possibility of association of congenital immunodeficiency with adenosine metabolism, the following hypothesis has been established from the discovery of defect of adenosinedeaminase in red blood cells of a hereditary disease patient who is substantially completely deficient in T and B cells. Deaminase defect-→Adenosine increase→Pyrimidine metabolism abnormality→Lymphocyte growth inhibition→Immunodeficiency (*Lancet*, 2, p. 1067, (1972)).

As described above, adenosine is now considered not as a mere metabolism product but as an important physiologically active substance having a messenger function between cells which acts on some targets or receptors. Accordingly, measurement of the adenosine content in living bodies under various physiological conditions or disease conditions is expected to be of significance even in the field of clinical medicine in connection with prevention, diagnosis and therapy of diseases, to say nothing about the field of basic research of medicine.

In the prior art, as the method for measurement of adenosine, some methods different in principle have been proposed. As one practical method of quantitative determination of adenosine in a living body sample, the enzymatic method is known (*Analytical Biochemistry*, 95, p. 377 (1977)). According to this method, adenosine in a living body sample is deaminated with adenosinedeaminase to form inosine, which is then reacted with purine nucleoside phosphorylase in the presence of phosphoric acid to obtain hypoxanthine and subsequently hypoxanthine is reacted with xanthineoxidase, and the hydrogen peroxide formed is quantitatively determined by the fluorescent method employing peroxidase. However, this method requires a cumbersome quantitative determination procedure due to a large number of reagent additions as well as many reaction steps involved, and there is also an additional disadvantage such as low sensitivity with the minimum measurement limit of 20 pmol/tube.

As another quantitative determination method, the binding protein method has been reported (*Analytical Biochemistry*, 85, p. 132-138 (1978)). This is a kind of competitive protein binding assay, in which adenine analog-binding protein is prepared from rabbit red blood cells and allowed to react competitively with $^3$H-adenosine and the adenosine in a sample. This method also has a drawback in that pre-treatment is required for isolation of adenosine in a sample by PEI cellulose column chromatography in performing assay because of the low specificity of the binding protein.

On the other hand, in recent years, immunoassays such as radioimmunoassay, enzyme immunoassay and fluorescence immunoassay have been developed as methods for quantitative determination of a trace substance in living bodies and applied for determination of various substances in living bodies. The immunoassay is based on the principle to determine quantitatively a subject substance to be measured in a sample by allowing the subject substance and a predetermined amount of labelled ligands to react competitively with a predetermined amount of antibodies, and thereafter measuring the quantity of the label of the labelled ligands bound to the antibodies or free (unbound) labelled ligands. In the prior art, as the method for preparation of the antigen of adenosine and its antibody, it is known to treat adenosine with sodium periodate to cleave oxidatively the linkage between the 2'-position and the 3'-position in ribose residue, then, after neutralization of excessive periodic acid with ethylene glycol, couple the cleaved product with bovine serum albumin (BSA) at a pH of 9 to 9.5 and stabilize the binding between the hapten and the BSA by reduction with sodium borohydride to give an antigen, which is in turn inoculated into a rabbit for immunization purposes to produce an antibody (*Proc. Natl. Acad. Sci. USA*, 52, p. 68 (1964)). A radioimmunoassay making use of the antibody produced by the periodate method mentioned above is reported in Pfluegers Archiv., 370, p. 167 (1978). The radioimmunoassay needs a purification procedure for adenosine in biological samples such as chromatography because of the low specificity of the antibody. The present inventors attempted to apply the antibody thus produced to radioimmunoassay, and subjected adenosine to antigen-antibody reaction against the antibody. As a result, it was found that adenosine had substantially no binding ability with this antibody and therefore application of this antibody to quantitative determination of adenosine was impossible. Further, it was also found that the binding reaction with the antibody could occur to enable immunoassay, when adenosine in a sample to be measured or radiolabelled adenosine was subjected to the same treatment as in the preparation of the antigen, namely the periodic acid treatment and the ethylene glycol treatment. However, this method requires two steps for pre-treatment of a sample, and also gives rise to the problem of instability of adenosine in the radioactive ligand and sample, thus failing to serve as a practical quantitative determination method of adenosine.

SUMMARY OF THE INVENTION

The present inventors have made various studies to establish a simple method of immunoassay with high sensitivity. As a consequence, the following findings were obtained:

(1) When adenosine is reacted with an acid anhydride such as succinic anhydride in an aqueous system or in a water-organic solvent system in the presence of an organic tert-amine, only the 2'- and 3'- hydroxyl groups among the $N^6$-amino group, the 2'-hydroxyl group, the 3'-hydroxyl group and the 5'-hydroxyl group all of which are subject to acylation were unexpectedly found to undergo acylation in preference to the other groups to give 2',3'-diacyladenosine at a yield of about 85% or higher under appropriate reaction conditions;

(2) Condensation of the product obtained by the acylation of adenosine with a dicarboxylic acid anhydride, for example, 2',3'-disuccinyladenosine, with a carrier protein using a condensing agent can give an antigen which, once inoculated into animals for immunization purposes, can produce highly sensitive anti-adenosine antibodies;

(3) The anti-adenosine antibodies thus prepared have no binding ability at all with adenosine, but on the other band have specific affinity for and high binding ability with 2',3'-diacyladenosine; and (4) Adenosine in a sample can be converted to 2',3'-diacyladenosine, which is in turn reacted with the above-described anti-adenosine antibodies together with labelled adenosine acylated at the 2'- and 3'-hydroxyl groups, whereby competitive antigen-antibody reactions occur depending on the respective concentrations, thus ensuring high sensitivity immunoassay.

These findings have been combined to accomplish the present invention.

The method of the present invention is a quantitative determination method of adenosine comprising the steps of:

(1) adding an acylating agent to a liquid sample and to a standard adenosine solution thereby acylating hydroxyl groups at the 2'-position and the 3'-position of each adenosine, (2) diluting each of the reaction mixtures which have undergone said acylation by addition of a buffer and then carrying out antigen-antibody reactions by mixing (a) each of these reaction mixtures with (b) a predetermined amount of labelled 2',3'-diacyladenosine and (c) a predetermined amount of anti-adenosine antibodies derived from an antigen comprising adenosine bound at the 2'- and the 3'-hydroxyl groups to a carrier protein through dicarboxylic acid residues;

(3) subsequently separating, in each of the reaction mixtures, free labelled adenosine from the labelled adenosine bound to the anti-adenosine antibody and measuring the quantity of the label in either one of the labelled adenosines to calculate the adenosine content in the sample therefrom.

According to the method of the present invention, in its most preferred embodiment, quantitative determination is possible with high sensitivity and accuracy within the measurement range of 0.125 to 64 pmol/tube. Further, no pre-treatment such as protein removal or isolation and purification of adenosine is required for a body fluid sample such as blood or urine, and with respect to a tissue sample, an acid extract can be subjected directly as it is to an assay according to the method of the present invention.

BRIEF DESCRIPTION OF THE DRAWING

FIG. 1 shows a calibration curve made in one example of the present invention, the ordinate axis indicating the bound percentage (B/T%) of antibody and the abscissa axis indicating adenosine concentration.

DETAILED DESCRIPTION OF THE INVENTION

The features and advantageous effects of the present invention will be described below in more detail following the procedures of the instant method.

(I) Preparation of samples to be assayed

Preparation of a living body sample is not particularly limited. A body fluid sample such as plasma, neurolymph, urine, etc. requires no pre-treatment but may be applied as such directly in the subsequent acylation reaction. But, in the case of a plasma sample, decomposition of adenosine with adenosinedeaminase or intake of adenosine by blood cells may proceed with the lapse of time after bloodletting to result in lowering of the adenosine content. In order to inhibit the activity of adenosinedeaminase, it is desirable to add an adenosinedeaminase inhibitor such as manganese ions, and also to add dipyridamole, lidocaine or benzyl alcohol in order to suppress intake by blood cells, immediately after bloodletting. Each reagent may be added in an amount which may be determined as desired depending on the type thereof, but manganese ions may be employed at a concentration of about 10 mM, while dipyridamole, lidocain or benzyl alcohol may be utilized at a level of about 0.01%, and 0.2 to 0.4% in a sample, respectively. Tissues in general may be subjected to protein removal and extraction with an acid (e.g. hydrochloric acid, perchloric acid, and trichloroacetic acid) and neutralized before application to acylation reaction.

(II) Preparation of anti-adenosine antibody

The anti-adenosine antibody to be used in the method of the present invention can be prepared by immunization of an animal with an antigen comprising adenosine bound at the 2'-position and 3'-position hydroxyl groups to a carrier protein through a dicarboxylic acid residue.

Typical examples of the dicarboxylic acid residue in the antigen include succinic acid residue, glutaric acid residue and the like. As the carrier protein, serum albumin, globulin, hemocyanin, ovalbumin, fibrinogen, etc. can be employed, but serum albumin is generally used.

Preparation of an antigen may be performed as follows:

(1) 2',3'-diacylation of adenosine:

Adenosine is allowed to react with an acid anhydride of dicarboxylic acids (e.g. succinic anhydride, glutaric anhydride, etc.) in water or a mixed water-organic solvent (e.g. pyridine, dioxane, acetone, acetonitrile, dimethyl sulfoxide, diethyleneglycol dimethylether, hexamethylphosphoric triamide, tetrahydropyran, tetrahydrofuran, methylcellosolve acetate, etc.) in the presence of an organic tert-amine (e.g. triethylamine, 4-morpholino-N,N'-dicyclohexylcarboxamine). The reaction can sufficiently proceed at room temperature within several seconds to ten and several minutes.

(2) Condensation between 2',3'-diacyladenosine and carrier protein:

Condensation reaction may be effected between the free carboxylic acid moieties of the acyl group residues of 2',3'-diacyladenosine and the amino groups in the carrier protein. The condensation reaction is not particularly limited, but there may be employed, for example, the carbodiimide method in which both the reactants are condensed in the presence of a carbodiimide reagent, including dicyclohexylcarbodimidie, 1-ethyl-3-(3- dimethylaminopropyl)-carbodiimide (EDC), 1-ethyl-3-(3-diethylaminopropyl)carbodiimide, 1-cyclohexyl-3-(2-morpholinoethyl)-carbodiimide, N-methyl-N,N'-di-t-butylcarbodiimidiumtetrafluoroborate, and the like. Further, there may also be employed the method in which Woodward reagent K is used as a condensing agent or the acid anhydride method. The condensation reaction may be conducted under the conditions according to a conventional manner.

The antibodies can be obtained by conventional immunization of an animal such as a rabbit, rat, ovine, horse or bovine with an antigen prepared in the manner described above. As the antibody, an antiserum obtained from an animal of the stated genus can be employed. The antibody can also be derived from an antiserum by purification, or alternatively from active fractions of an antibody such as the F(ab')$_2$ fragment obtained by enzymatic treatment of the antibody, for example, with pepsin, and the Fab' fragment obtained by further treatment with a reducing agent such as 2-mercaptoethylamine.

It is also possible to use monoclonal antibodies obtained by subjecting antibody-producing cells of an immunized animal and myeloma cells to cell fusion according to a known method and proliferating the resultant hybridoma in vitro or in vivo.

Further, while the antibody for use in an assay in accordance with the liquid phase method may be prepared in the form of various buffer solutions or lyophilized products, it may be prepared by immobilization on an insoluble carrier for use in an assay in accordance with the solid phase method.

As the insoluble carrier on which the antibody is immobilized, those generally employed in immunoassays may be applied including silicones, glass, ceramics, polystyrenes, styrene-divinylbenzene copolymers, polyethylenes, polypropylenes, crosslinked polyacrylamide, CM cellulose, DEAE cellulose, and crosslinked dextran. The shape of the carrier is not limited but may be in any form such as latexes, granules, and tubes. Immobilization of the antibody on the insoluble carrier may also be conducted according to a well known method, for example, by direct physical adsorption onto the carrier or by chemical bonding through a bifunctional chemical binder such as glutaraldehyde, 2,2-dipyridyl-sulfide, and p,p'-difluoro-m,m'-dinitrodiphenylsulfone.

(III) Preparation of labelled 2',3'-diacyladenosine

As the labels for labelled 2',3'-diacyladenosine, those which are commonly used as labels in immunoassays and capable of labelling adenosine such as radioisotopes, enzymes, fluorescent substances and chemical luminescent substances can be applied. Examples of radioisotopes for labelling are $^3$H, $^{125}$I and $^{131}$I, enzymes for labelling are β-galactosidase, alkaline phosphatase, peroxidase, glucoseoxidase and the active fragments thereof, and fluorescent substances for labelling are fluorescein and Rhodamine. Labelling with these substances can be effected in accordance with a conventional labelling method.

When $^3$H is used as a label, for instance, a commercially available $^3$H-adenosine which has been subjected to acylation at the 2'-position and 3'-position hydroxyl groups thereof may be used. The type of the acyl group to be introduced may be selected depending on the type of the dicarboxylic acid residue at the binding moiety between the antigen hapten and the carrier protein employed for preparation of the antibody. For example, when the antigen has a succinic acid residue, a succinyl group may be most preferably selected. It is also possible to use other acyl groups similar in structure to succinyl group such as acetyl group, propionyl group, butyryl group, and glutaryl group, although measurement sensitivity of assay may slightly be lowered. Acylation may be performed under the conditions as described in the preparation of the antigen. Acylation of the labeled ligand may be conducted in performing assay at the same time as acylation of the sample to be measured.

When radioactive iodine is used as a label, there may be employed a method wherein dicarboxylic acid residues are introduced as acyl groups into the 2'- and 3'-hydroxyl groups of adenosine and to the free carboxylic acid moieties are further bound tyrosine methyl esters for labelling the benzene rings thereof with the radioactive iodine.

(IV) Acylation of sample and standard solution

Acylation reaction is conducted similarly as in the acylation of adenosine described above with reference to the preparation of an antigen. Acylation is thus carried out by adding an acid anhydride and an organic tert-amine to a sample and to a standard solution.

The species of the acid anhydride may be determined similarly as the acyl group in the 2',3'-diacyladenosine. In the acylation of a sample and a standard solution, it is preferred from the viewpoint of the quantitative determination procedure to prepare the acid anhydride in a predetermined reagent form. The acid anhydride may be formulated in powder form, but more preferably be formulated previously as a solution in an organic solvent since the solution has better miscibility with the organic tertamine and the sample, and easy in handling. The organic solvent and the organic tertiary amine to be employed are also to be selected as discussed previously. When the acid anhydride and organic tert-amine are allowed to be co-present in the same solvent solution, both will react with each other, whereby the acylating ability of these reagents will be reduced to half of the original ability after an elapse of 24 hours. Accordingly, when both reagents are incorporated in a reagent kit for which stability of the reagents is required, they should be packed separately from each other.

The amount of the reagent may suitably be determined depending on the species of the reagent. For example, there may be employed 100 μl of a reagent comprising 20 to 40 μmol of an acid anhydride, 5 to 10 μl of an organic tert-amine and a remainder of an organic solvent.

The acylating reaction can be carried out under the conditions of room temperature and the period ranging from several seconds to ten and several minutes. For example, when a physiological saline solution to which 5 μmol of adenosine has been added or some other samples were subjected to succinylation, the yields of 2',3'-disuccinyladenosine determined by high speed liquid chromatography were obtained as shown in Table 1.

TABLE 1

| Species of samples (living body components in 100 μl) | Yield (%) |
|---|---|
| Physiological saline solution | 88.0 |
| Rat plasma (90 μl) | 87.3 |
| Rat urine (90 μl) | 85.0 |
| Human plasma (90 μl) | 85.2 |
| Human urine (90 μl) | 85.5 |
| Rat liver acid extract (20 mg) | 86.5 |
| Rat heart acid extract (22 mg) | 87.1 |

TABLE 1-continued

| Species of samples (living body components in 100 μl) | Yield (%) |
|---|---|
| Rat brain acid extract (25 mg) | 88.4 |

(V) Antigen-antibody reaction

After acylation, each sample to be measured is diluted generally to 5 to 6 times with a buffer. The adenosine standard solution is diluted successively by twice with a buffer for dilution (usually a buffer containing 5 to 10% of an acylating reagent) to be provided for use in the antigen-antibody reactions.

As the buffer, any buffer that can promote a stable antigen-antibody reaction may be applicable. In the method of the present invention, a 0.1 to 0.5 M imidazole buffer of a pH of 5 to 8 is particularly preferred. If attempts are made to enable substantial removal of the effects of non-specific factors or unreacted acylating reagent used which inhibit the antigen-antibody reaction, there may also be employed other buffers such as acetate buffer, citrate buffer and phosphate buffer.

The antigen-antibody reaction may be carried out by adding simultaneously or sequentially the 2',3'-diacyladenosine in the sample to be measured and a predetermined amount of the labelled 2',3'-diacyladenosine to a predetermined amount of a soluble or insoluble anti-adenosine antibody. The chemical quantity of the labelled 2',3'-diacyladenosine may most preferably be 0.5 to 1 pmol in the case of $^3$H-2',3'-disuccinyladenosine.

The antigen-antibody reaction is carried out ordinarily at 0° to 10° C. for 6 to 48 hours, preferably for 12 to 24 hours.

(VI) Measurement

After completion of the antigen-antibody reaction, the labelled 2',3'-diacyladenosine bound to the antibody (hereinafter referred to as "B") is separated by a conventional method from the free labelled 2',3'-diacyladenosine not bound to the antibody (hereinafter referred to as "F"), and either one of them is subjected to measurement of the quantity of the label.

In the solid phase method, separation between "B" and "F" can easily be done by suction, decantation, filtration and other known methods. In the liquid phase method, "B" and "F" can be separated from each other by a method in which an appropriate separating agent is employed. As applicable methods, there may be included, for example, a double antibody method in which a second antibody against the anti-adenosine antibody or F(ab')$_2$ or Fab' fragment thereof is prepared by immunization of an animal different in species from that used in preparation of the first antibody, and the resultant second antibody is caused to adsorb and precipitate "B"; or in which a second antibody is immobilized onto a suitable insoluble carrier and "B" is bound thereto; a method in which "F" is separated by adsorption with an activated carbon coated with dextran (DCC); a method in which "B" is separated by precipitation with polyethylene glycol; the salting-out method in which "B" and "F" are fractionated using ammonium sulfate. The separation procedures with the use of these separating agents may be conducted in conventional manners, respectively. For example, in the case of DCC, DCC may be added to a reaction mixture which has been subjected to an antigen-antibody reaction, followed by centrifugation, whereby "B" can be recovered as the supernatant which is subjected to measurement of the quantity of the label.

The quantity of the label can be measured by a suitable known method depending on the species of the label. For example, measurement of the quantity of radioactivity may be performed by means of an instrument which can measure the quantity of the radioactive element used as the label, such as a liquid scintillation counter or a gamma counter.

The quantity of the enzyme can be obtained by measuring the quantity or rate of the consumption and production of substances resulting from enzymolysis by an electro-chemical, spectroscopic or fluorescent method in a substrate solution corresponding to the species of the particular enzyme selected.

The adenosine content in a biological sample can be determined by determining the bound percentage = B/T (%) from the measured radioactivity according to the formula shown below, and plotting the B/T (%) values on a calibration curve made by plotting the B/T (%) values determined similarly from the measured radioactivity of the standard solutions of various concentrations as ordinate versus the concentration as logarithmic abscissa.

$$B/T(\%) = \frac{(B) - (BL)}{(T) - (BL)} \times 100\,(\%)$$

wherein (B) is an average quantity of label of the biological sample or the respective starndard solutions, (BL) is an average value of blank, and (T) is an average value of total quantity of the label.

The validity of the measurement of biological samples according to the method of the present invention is shown below by the dilution, addition experimental results. The quantitative determination operations were conducted according to the same procedure under the same conditions, using the same reagents, as in the Examples set forth hereinafter.

(1) In case of plasma samples
(n=3, average value±standard error)

TABLE 2

| Dilution (times) | Adenosine added (pmol/tube) | Measured values (pmol/tube) | Recovery (%) |
|---|---|---|---|
| 1 | — | 10.4 ± 0.2 | — |
| 2 | — | 5.3 ± 0.1 | — |
| 2 | 5.0 | 10.4 ± 0.2 | 101.0 |
| 4 | — | 2.7 ± 0.1 | — |
| 4 | 2.5 | 5.1 ± 0.2 | 98.1 |

(2) In case of liver extract
(n=3, average value±standard error)

TABLE 3

| Dilution (times) | Adenosine added (pmol/tube) | Measured values (pmol/tube) | Recovery (%) |
|---|---|---|---|
| 1 | — | 8.6 ± 0.2 | — |
| 2 | — | 4.4 ± 0.2 | — |
| 2 | 5.0 | 9.8 ± 0.4 | 104.3 |
| 4 | — | 2.3 ± 0.2 | — |
| 4 | 2.5 | 5.0 ± 0.3 | 104.2 |

The present invention will now be described in further detail with reference to the following Example, which is presented as illustrative of an embodiment of the present invention and not intended to limit the scope of the present invention.

EXAMPLE

(1) Preparation of reagents for quantitative determination (i) Preparation of an antigen for use in the preparation of anti-adenosine antibody To a solution of 6.7 g of adenosine dissolved in 500 ml of distilled water were added 20 g of succinic anhydride, 450 ml of dioxane and 50 ml of triethylamine, and the resultant mixture was stirred at room temperature for 10 minutes to cause reaction. The reaction was stopped by adding one liter of distilled water to the reaction mixture, which was concentrated under reduced pressure. The residue was then dissolved in water and the crystals precipitated on cooling were collected by filtration. The crude crystals were recrystallized from water-ethanol-dioxane and dried to give 6.80 g of 2',3'-disuccinyl-adenosine.

melting point: 192.2° C.
Nuclear Magnetic Resonance Spectrum (NMR)δ(ppm) (DMSO-$d_6$)
8.31, 8.13 (each 1H, s, H -2 or H-8), 7.37 (2H, bs, $NH_2$), 6.21(1H, d, H-1'), 5.90(1H, t, H-2'), 5.51(1H, m, H-3'), 4.20(1H, m, H-4'), 3.67(2H, bd, H-5'), 2.30–2.75 (8H, m,

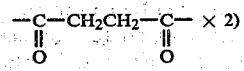
$\times 2$)

An acetate buffer (pH 5.5) was added to 200 mg of 2',3'-disuccinyladenosine, 100 mg of human serum albumin and 100 mg of EDC (hydrochloride) to make up a total volume of 30 ml, and the reaction was carried out at room temperature for 20 hours. The reaction mixture was dialyzed at 4° C. against a flow of 20 liters of a 0.9% physiological saline solution for 48 hours. The molar ratio of 2',3'-disuccinyladenosine to human serum albumin obtained from UV-absorption spectrum of the dialysate was 10.6.

(ii) Preparation of anti-adenosine antibody

The above antigen solution was mixed with an equal volume of complete Freund's adjuvant and administered as a water-in-oil emulsion intradermally at the back skin of a house rabbit at a dose of 0.2 mg as albumin amount three times every 10 days and after 30 days administration was further repeated twice. After bloodletting, the serum obtained by centrifugation was diluted with 50 mM acetate buffer (pH 6.5) to provide anti-adenosine antibody reagent.

(iii) Preparation of radiolabelled 2',3'-disuccinyl adenosine (2, 8-$^3$H) adenosine (produced by NEN Co.; specific radioactivity: 35.2 Ci/mmol) was diluted to 100 times with 50 mM acetate buffer, and 1 ml of the resultant solution was mixed with 40 mg of succinic anhydride, 0.9 ml of dioxane and 0.1 ml of triethylamine to carry out the reaction at room temperature for 5 minutes. After the reaction, 38 ml of 0.3 M imidazole buffer (pH 6.5) was added to the reaction mixture to finally form 10 ml of $^3$H-2',3-dissuccinyladenosine 2.5 μCi/0.3 M imidazole buffer (pH 6.5) to provide a $^3$H-2',3'-disuccinyladenosine reagent.

(iv) Preparation of a sample to be measured

To the blood let from a rat of the SD strain, 10 mM manganese chloride and 4 mg/ml of benzyl alcohol were added and the supernatant obtained by centrifugation of the mixture was provided as a plasma sample.

(v) Preparation of succinylating reagent

A succinylating reagent was prepared by mixing 400 mg of succinic anhydride and 9 ml of dioxane with 1 ml of triethylamine.

(vi) Preparation of a buffer for dilution

A buffer for dilution was prepared by mixing 0.3 M imidazole buffer (pH 6.5), distilled water and a succinylating reagent at a ratio of 8:1:1.

(vii) Preparation of a reagent for BF separation

DCC was prepared by mixing 500 mg of active carbon, 500 mg of bovine serum albumin and 75 mg of dextran in 50 ml of distilled water and a two-fold diluted solution thereof was provided as a reagent for separation.

(2) Quantitative determination procedure (i) Succinylation of sample and standard solution One hundred (100) μl of an adenosine solution (6,400 pmol/ml water) was sampled in a small test tube, mixed with 100 μl of a succinylating reagent, and the mixture was left to stand at room temperature for 5 minutes. Then, 800 μl of 0.3 M imidazole buffer (pH 6.5) was added to the mixture to prepare 1 ml of a standard solution (No.I) of 2',3'-disuccinyladenosine (64 pmol/100 μl)

500 μl each of aliquots of the buffer for dilution was apportioned into 9 small test tubes (No. II-X), and 500 μl of the standard 2',3'-disuccinyladenosine solution was added to the small test tube of No. II, followed by mixing. Subsequently, two-fold dilutions were successively conducted to prepare 2',3'-succinyladenosine standard solutions at the respective concentrations ( /100 μl) shown below:

64 pmol (No. I), 32 pmol (No. II)
16 pmol (No. III), 8 pmol (No. IV)
4 pmol (No. V), 2 pmol (No. VI)
1 pmol (No. VII), 0.5 pmol (No. VIII)
0.25 pmol (No. IX), 0.125 pmol (No. X)

Into a small test tube was charged 100 μl of a plasma sample which was then admixed with 100 μl of a succinylating reagent. The mixture was left to stand at room temperature for 5 minutes and then 800 μl of 0.3 M imidazole buffer (pH 6.5) was added thereto.

(ii) Antigen-antibody reaction

Small test tubes were prepared as follows:

| For total count: | Two | Nos. 1 & 2 |
| For Blank: | Two | Nos. 3 & 4 |
| For Zero: | Two | Nos. 5 & 6 |
| For standard solutions: | Twenty | Nos. 7-26 |
| For plasma samples: | Two | Nos. 27 & 28 |

100 μl each of aliquots of $^3$H-2',3'-disuccinyladenosine reagent was apportioned into the test tubes No. 1 to No. 28.

To each of the test tubes for total count (Nos. 1 & 2), for Blank (Nos. 3 & 4) and for Zero (Nos. 5 & 6), 100 μl of the buffer for dilution was added.

To each of the test tubes for standard solutions (Nos. 7-26), 100 82 1 of the 2',3'-disuccinyladenosine standard solutions Nos. I-X was added, respectively.

To the test tubes for plasma samples (Nos. 27, 28) was added 100 μl each of the succinylated plasma sample.

To each of the test tubes for Zero, Standard solutions and Plasma samples (Nos. 5-28), 100 μl of the antiadenosine antibody reagent was added, and after mixing each test tube was left to stand in an ice-water bath for 18 hours.

To each of the test tubes for Total count and Blank (Nos. 1–4), 100 μl of 0.3 M imidazole buffer was added and after mixing each test tube was left to stand in an ice-water bath for 18 hours.

(iii) Measurement of radioactivity quantity and calculation of adenosine content To the test tubes except those for Total count was added 500 μl each of the reagent for separation, followed by centrifugation at 3000 rpm for 5 minutes.

To each of the test tubes for Total count was added 500 μl of water, followed by mixing.

From each test tube 500 μl of supernatant was sampled, transferred into a test tube for measurement of radioactivity in which each radioactivity was measured by means of a liquid scintillation counter (produced by Aloka Co., Liquid Scintillation Spectrometer).

The bound percentages B/T (%) were calculated based on the measured values to obtain the results as shown in Table 4.

TABLE 4

| Measured samples | Average count (B) (cpm) | (B) - (BL) | B/T (%) |
|---|---|---|---|
| Blank (BL) | 256 | — | |
| Total count (T) | 10751 | 10495 | 100.0 |
| Zero | 5677 | 5421 | 51.6 |
| Standard solution: | | | |
| 0.125 pmol | 5436 | 5180 | 49.4 |
| 0.25 pmol | 5083 | 4827 | 46.0 |
| 0.5 pmol | 4708 | 4452 | 42.4 |
| 1 pmol | 3675 | 3419 | 32.6 |
| 2 pmol | 2714 | 2458 | 23.4 |
| 4 pmol | 1851 | 1595 | 15.2 |
| 8 pmol | 1166 | 910 | 8.7 |
| 16 pmol | 719 | 463 | 4.4 |
| 32 pmol | 522 | 266 | 2.5 |
| 64 pmol | 382 | 126 | 1.2 |
| Plasma sample | 2251 | 1995 | 19.0 |

From these values, the calibration curve (see FIG. 1) was made and the adenosine contents in the plasma sample was determined using this curve. The value was found to be 2.8 pmol/tube, 280 pmol/ml plasma.

We claim:

1. A method for determining quantitatively the adenosine content in a sample by immunoassay, comprising the steps of:
   (1) adding an acylating agent to a liquid sample and to a standard adenosine solution thereby acylating hydroxyl groups at the 2'-position and the 3'-position of each adenosine;
   (2) diluting each of the reaction mixtures which have undergone said acylation by addition of a buffer and then carrying out antigen-antibody reactions by mixing (a) each of these reaction mixtures with (b) a predetermined amount of labelled 2',3'-diacyladenosine and (c) a predetermined amount of anti-adenosine antibodies derived from an antigen comprising adenosine bound at the 2'- and the 3'-hydroxyl groups to a carrier protein through dicarboxylic acid residues; and
   (3) subsequently separating, in each of the reaction mixtures, free labelled adenosine from the labelled adenosine bound to the anti-adenosine antibody and measuring the quantity of the label in either one of the labelled adenosines to calculate the adenosine content in the sample therefrom.

2. A method according to claim 1, wherein the dicarboxylic acid residue which binds the adenosine to the carrier protein in the antigen for obtaining the anti-adenosine antibody is a succinic acid residue.

3. A method according to claim 1, wherein the acylating agent comprises an acid anhydride and an organic text-amine.

4. A method according to claim 3, wherein the acid anhydride is succinic anhydride.

5. A method according to claim 1, wherein the labelled 2',3'-diacyladenosine is a labelled 2',3'-disuccinyladenosine.

6. A method according to claim 1, wherein the label is a radioactive element, enzyme, fluorescent substance or chemical luminescent substance.

* * * * *